(12) United States Patent
Storberg et al.

(10) Patent No.: US 10,046,072 B2
(45) Date of Patent: Aug. 14, 2018

(54) DRAIN SYSTEM FOR A STERILIZATION APPARATUS

(75) Inventors: Bengt Storberg, Falkenberg (SE); Stefan Troedsson, Ullared (SE)

(73) Assignee: GETINGE STERILIZATION AB, Getinge (SE)

( * ) Notice: Subject to any disclaimer, the term of this patent is extended or adjusted under 35 U.S.C. 154(b) by 350 days.

(21) Appl. No.: 14/403,629

(22) PCT Filed: Jun. 18, 2012

(86) PCT No.: PCT/EP2012/061610
§ 371 (c)(1),
(2), (4) Date: Jan. 7, 2015

(87) PCT Pub. No.: WO2013/189515
PCT Pub. Date: Dec. 27, 2013

(65) Prior Publication Data
US 2015/0125349 A1 May 7, 2015

(51) Int. Cl.
*A61L 2/07* (2006.01)
*A61L 2/04* (2006.01)
*A61L 2/18* (2006.01)

(52) U.S. Cl.
CPC .......... *A61L 2/07* (2013.01); *A61L 2/04* (2013.01); *A61L 2/18* (2013.01); *A61L 2202/121* (2013.01); *A61L 2202/123* (2013.01)

(58) Field of Classification Search
CPC ..... A61L 2/07; A61L 2/18; A61L 2/04; A61L 2/20; A61L 2/204; A61L 2202/121; A61L 2202/123; A61L 2202/14
See application file for complete search history.

(56) References Cited

U.S. PATENT DOCUMENTS 4,781,898 A 11/1988 Jones
5,195,048 A * 3/1993 Chiffon .................. A61L 2/07
137/12

(Continued)

FOREIGN PATENT DOCUMENTS

CN 200986366 Y 12/2007
DE 202010006264 U1 9/2010

(Continued)

OTHER PUBLICATIONS

Chinese Office Action dated Mar. 3, 2016.
(Continued)

*Primary Examiner* — Timothy C Cleveland
(74) *Attorney, Agent, or Firm* — Aaron M. Miller (57) ABSTRACT

A sterilization apparatus is disclosed for sterilization of objects. The sterilization apparatus includes a chamber for receiving the objects, the chamber including a sterilization medium inlet and outlet; an inlet flow control device for controlling a supply of a sterilization medium to the chamber; a drain system for controllable discharge of fluid from the chamber; and a control unit configured to control the inlet flow control device and drain system in accordance with a sterilization scheme. The drain system includes: a drain inlet connected to the sterilization medium outlet; a drain outlet connected to a vacuum system for evacuating the chamber; a first conduit connecting the drain inlet and outlet; and a proportional valve, arranged along the first conduit, controllable by the control unit to partly restrict fluid flow through the first conduit according to a continuous relation between a control parameter and a valve opening of the proportional valve.

20 Claims, 3 Drawing Sheets

(56) References Cited

U.S. PATENT DOCUMENTS

| | | | |
|---|---|---|---|
| 6,729,601 B2* | 5/2004 | Freisinger | G05D 16/2093 |
| | | | 251/129.05 |
| 2002/0068012 A1* | 6/2002 | Platt, Jr. | A61L 2/14 |
| | | | 422/22 |
| 2005/0249650 A1 | 11/2005 | Johannes Damhuis et al. | |
| 2007/0258855 A1 | 11/2007 | Turcot et al. | |
| 2013/0084225 A1* | 4/2013 | Buczynski | A61L 2/07 |
| | | | 422/292 |

FOREIGN PATENT DOCUMENTS

| | | |
|---|---|---|
| EP | 0079693 A2 | 5/1983 |
| EP | 2100622 A2 | 9/2009 |
| JP | S5891358 A | 5/1983 |
| JP | 2005218548 A | 8/2005 |
| JP | 2007252651 A | 10/2007 |
| JP | 2010259482 A | 11/2010 |
| JP | 2011200468 A | 10/2011 |
| WO | WO-2000078365 A1 | 12/2000 |
| WO | WO-2001058498 A1 | 8/2001 |
| WO | WO-2005113024 A1 | 12/2005 |
| WO | WO-2008052332 A1 | 5/2008 |

OTHER PUBLICATIONS

International Search Report PCT/ISA/210 for International Application No. PCT/EP2012/061610 dated Nov. 13, 2012.
Written Opinion of the International Searching Authority PCT/ISA/237 for International Application No. PCT/EP2012/061610 dated Nov. 13, 2012.

* cited by examiner

DRAIN SYSTEM FOR A STERILIZATION APPARATUS

TECHNICAL FIELD OF THE INVENTION

The present invention relates to a sterilization apparatus for sterilization of objects by means of a sterilization fluid, such as e.g. steam.

BACKGROUND OF THE INVENTION

A common technique to sterilize objects used in e.g. hospitals, laboratories and the pharmaceutical industry is to use a sterilization apparatus such as an autoclave. A sterilization apparatus typically comprises a chamber for receiving the objects to be sterilized, a fluid system for supplying a sterilization medium to the objects inside the chamber and a drain system or vent path for discharging the sterilization medium out from the chamber.

In steam sterilization, steam is introduced into the chamber and the temperature is increased to a sterilization temperature. After a predefined sterilization time, which depends on the sterilization temperature used, the steam is evacuated from the chamber through the drain system. The steam may then be condensed and discharged from the system. These above-mentioned process steps may be referred to as a process cycle or a process scheme.

The discharge of sterilization medium from the chamber to the drain system is designed to conform to the other steps in the process cycle. Therefore the discharge of sterilization medium from the chamber to the drain system is adapted to a certain sterilization chamber and a certain sterilization process cycle. However, in some cases there is a need for increasing or decreasing the discharged flow.

U.S. Pat. No. 4,781,898 discloses a sterilization pressure chamber of an autoclave with two valve controlled vent paths. A first vent path channels the sterilizing steam from the chamber into a condensing coil having an end which opens into a liquid reservoir. When the pressure within the chamber drops to a predetermined level, a second vent path, having a flow rate which is greater than the first path, opens and provides a channel for the rapid escape of the remainder of the steam from the chamber. Hence, the autoclave may be vented in a faster manner.

It would be desirable to provide a sterilization apparatus where the drain system is able to discharge the sterilization fluid from the chamber in an even faster manner.

SUMMARY

An object of the invention is to overcome the above problems, and to provide a sterilization apparatus and a drain system which provide for faster process cycles without damaging the load or its packaging material.

This and other objects, which will become apparent in the following, are accomplished by means of a sterilization apparatus defined in the accompanying claims.

According to a first aspect of the invention, a sterilization apparatus for sterilization of objects is provided. The sterilization apparatus comprises:

a chamber for receiving the objects to be sterilized, the chamber having a sterilization medium inlet and a sterilization medium outlet;

an inlet flow control device connected to the sterilization medium inlet for controlling a supply of a sterilization medium to the chamber;

a drain system connected to the sterilization medium outlet of the chamber for controllable discharge of fluid from the chamber; and a control unit connected to the inlet flow control device and the drain system and configured to control the inlet flow control device and the drain system in accordance with a predefined sterilization scheme;

wherein the drain system comprises:

a drain inlet connected to the sterilization medium outlet of the chamber;

a drain outlet connected to a vacuum system for evacuating the chamber;

a first conduit connecting the drain inlet and the drain outlet; and a proportional valve arranged along the first conduit, the proportional valve being controllable by the control unit to partly restrict fluid flow through the first conduit according to a predefined continuous relation between a control parameter and a valve opening of the proportional valve.

The present invention is based on the realization that by providing a drain system comprising a proportional valve, the fluid flow through the drain system may be controlled in a continuous manner, thus providing a faster and better controlled discharge of fluid from the chamber. By providing a proportional valve, the number of valves in the drain system may be reduced as the proportional valve may provide for a precise control of the flow through the first conduit over a wide flow range. For example, if the predefined sterilization scheme is designed to admit a relatively small fluid flow to be discharged from the chamber during a certain time in the process, and a relatively large fluid flow to be discharged from the chamber during another time in the process, a drain system with more than one digital valve is needed in order to adapt the drain system for the different discharged flows. By using a proportional valve, the number of valves used may be minimized. Hereby, the manufacturing cost of the drain system may be reduced since fewer components are needed. The present invention is further based on the realization that by controlling the proportional valve according to a predefined continuous relation between a control parameter and the valve opening of said proportional valve, the predefined sterilization scheme may be made to conform to boundary conditions, or constraints, by admitting a continuous fluid flow through the drain system, providing a fast and controlled discharge of fluid out from the chamber.

During the introduction or discharge of fluid to and/or from the chamber, the pressure inside the chamber will change. If the pressure inside the chamber changes too fast, the pressure change may cause harm to components inside the sterilization apparatus and/or objects inserted into the chamber. Owing to this problem, technical standards with pressure change requirements have been compiled. For example, the technical standard EN285 (European standard) states that the average pressure change for any 3 s interval during the sterilization cycle shall not exceed 1000 kPa/min. Therefore, the rate of pressure change in the sterilization scheme is adapted to comply with the regulations.

Moreover, if fluid is being discharged from the chamber the resulting pressure drop may cause fluids inside the chamber to boil. For example, if an open container containing fluid is to be sterilized, the pressure drop may cause the fluid inside the container to boil and be spattered inside the chamber. Thus, loss of potentially valuable fluid may occur.

When using a digital valve to reduce the pressure inside the chamber, a method where the valve is alternating between an open state and a closed state for gradually"

lowering the pressure inside the chamber in a stepwise manner may be used. However this method is associated with valve control difficulties. For example, since pressure drop in the beginning of the discharge process is changing rapidly with a movement of the valve, the dynamics of the valve needs to be very fast and/or the opening of the valve needs to be very small in order for the pressure drop to be acceptable. Furthermore, in the end of the discharge process, the pressure difference between inside and outside of the chamber is lower and the pressure reduction is less sensitive for a movement of the valve. Thus, it is preferred to have a large valve opening in order to quickly discharge the remaining fluid from the chamber. This problem may be solved by having valves with different sizes and/or different dynamic behaviour.

In order to comply with the above mentioned requirements for the rate of pressure change, and to avoid too large pressure drops inside the chamber, the dynamics of the valve opening and valve closing are time-averaged in accordance with the requirements. However, there might still occur pressure drops which instantaneous lower the pressure below the requirements for the rate of pressure change, since the reduction in pressure inside the chamber is carried out in a stepwise manner. Furthermore, using time-averaged behaviour of the valve implies that a safety margin to the requirements for the rate of pressure change needs to be applied. Hence, the process time for discharging fluid from the chamber is unnecessary long.

By using a proportional valve, there is no need to time-average the dynamic behaviour of the valve, instead it is possible to comply with the requirements for the rate of pressure change in a continuous manner. Also, by using a proportional valve, the valve opening may be very large in a fully open state and thus allow for a rapid discharge of fluid from the chamber during the end of the discharge process, while still being small enough for a controllable outlet flow in the beginning of the discharge process. Thus, the process may be carried out in a faster manner and the utilization of fluids may be higher, thereby reducing costs.

The predefined sterilization scheme may comprise the steps of evacuating air from the chamber, introducing the sterilization medium to the chamber, and evacuating the sterilization medium and/or air and/or another fluid from the chamber. It should be understood that the sterilization medium provided to the chamber may be steam, superheated water, formalin and/or formaldehyde. The fluid discharged from the system may be the sterilization medium, air and/or any other fluid present in the chamber.

During either the evacuating of fluid from the chamber or the introduction of sterilization medium into the chamber, the inlet flow control device and/or the drain system is controlled by the control unit to admit sterilization medium into and/or fluid out of the chamber. For example, if the control unit controls the proportional valve in the drain system to restrict flow out of the chamber, and the control unit controls the inlet flow control device to admit flow into the chamber, the pressure and/or temperature in the chamber will increase. On the other hand, if the control unit controls the inlet flow control device to restrict flow into the chamber, and the control unit controls the proportional valve in the drain system to discharge flow out of the chamber the pressure and/or temperature in the chamber will decrease. A scenario is also possible where the control unit controls both the inlet flow control device and the proportional valve in the drain system allowing flow both into and out of the chamber simultaneously or subsequently.

The inlet flow control device may e.g. be a conventional valve such as a digital valve. It should be noted that the inlet flow control device may comprise any type of valve or device being able to admit a fluid flow to the chamber in a controllable manner.

It should be understood that the vacuum system is for evacuating the chamber. This may be achieved by providing a lower pressure outside the chamber compared to inside the chamber, thus allowing fluid to be discharged from the chamber. According to one embodiment of the invention, the vacuum system comprises a heat exchanger, such as e.g. a condenser. The condenser may cool and/or condensate the discharged fluid from the chamber by using a flow of coolant. For example, if the fluid discharged from the chamber is steam, condensing the steam in the condenser by using the flow of coolant will result in volume change of the fluid and thus, a lower pressure outside the chamber compared to inside the chamber. The vacuum system may comprise a pump, such as e.g. a vacuum pump. The pump may then provide for the lower pressure outside the chamber compared to inside the chamber. The vacuum system may comprise both a heat exchanger, such as e.g. a condenser, and a pump, such as e.g. a vacuum pump.

Accordingly, various embodiments of the present invention provide drain systems which are able to discharge fluid from the chamber of the sterilization apparatus in a continuous manner using a proportional valve.

The sterilization apparatus may comprise a sterilization medium providing device connected to the sterilization medium inlet for providing the sterilization medium to the chamber. The sterilization medium providing device may e.g. be a steam generator.

The control unit may be connected to other parts and devices in the sterilization apparatus other than the inlet flow control device and the proportional valve in the drain system. The control unit may be connected to the chamber for e.g. detecting the pressure inside the chamber. Thus, according to at least one embodiment of the sterilization apparatus of the present invention, the control parameter may be based on a pressure inside the chamber. Thus, the chamber may be provided with a pressure sensor connected to the control unit. Hereby, the control system may control the pressure inside the chamber in such way that the pressure increases or decreases in accordance with the predefined sterilization scheme. For example, if the pressure inside the chamber is to be increased, the control unit may control the inlet flow control device to admit more sterilization medium into the chamber. Likewise, if the pressure inside the chamber is to be decreased, the control unit may control the proportional valve in the drain system to admit more fluid to be discharged from the chamber.

The control unit may also be connected to the vacuum system. According to at least one embodiment, the vacuum system is arranged to cool the evacuated fluid using a flow of coolant, and the control parameter may be based on a temperature of the coolant. The vacuum system and/or the flow of coolant may be provided with a temperature sensor connected to the control unit. The temperature sensor may be connected to the flow of coolant leaving the vacuum system. Hereby, the temperature of the coolant may be controlled such that it is kept within a desired range. For example, if the temperature of the coolant is approaching a maximum allowable temperature, the control unit may control the proportional valve in the drain system to restrict the discharge of fluid out of the chamber. It is also within the scope of the present invention that the control unit may be detecting various parameters, such as e.g. both the pressure inside the chamber and the temperature of the coolant, in order to operate the sterilization apparatus in accordance with the predefined sterilization scheme.

Furthermore, the control unit may be connected to the sterilization medium providing device for optimizing the supply of sterilization medium in accordance with the predefined sterilization scheme. It should be noted that the control unit may be connected to any suitable part or device of the sterilization apparatus. Hereby, the control unit may control the sterilization apparatus in accordance with the predefined sterilization scheme in different ways.

In embodiments of the present invention, the drain system may further comprise a second conduit separated from the first conduit, connecting the drain inlet and the drain outlet, and a further valve arranged along the second conduit to allow control of a flow through the second conduit. Hereby, an additional path for controlling the discharge of fluid out from the chamber is introduced. Thus, the further valve may be open to admit discharge of fluid from the chamber regardless of whether the proportional valve is open, closed or partly closed.

Furthermore, a cross section of the second conduit may be substantially smaller than a cross section of the first conduit. Each of the cross sections may be a cross-sectional area perpendicular to a main direction of a fluid flow, in each of the first and the second conduit. Furthermore, the second conduit may be provided with a throttle. Hereby the flow through the second conduit may be adapted to be relatively small compared to flow through the first conduit, while still providing for an evacuation path for steam and/or condensate from the chamber. Thus, the control of discharged fluid from the system may be facilitated.

According to at least one embodiment of the present invention, the proportional valve comprises a movable part and a controllable actuator connected to the movable part for controlling a position of the movable part between a closed state and a fully open state. Thus, the proportional valve is configured to allow various fluid flows through the drain system. For example, in the closed state, the movable part restricts all flow through the first conduit and sterilization medium may be introduced into the chamber, increasing the pressure inside the chamber. On the other hand, in the fully open state, the movable part allows flow through first conduit and the pressure inside the chamber may be reduced. In the fully open state, a relatively large flow may be discharged from the chamber since the valve opening may be large. Thus quick discharge of the remaining fluid from the chamber is possible, even though the difference in pressure inside and outside of the chamber is small. This implies that the process time may be fast and that the utilization of fluids may be high.

In embodiments of the present invention the proportional valve may be configured in such a way that a given change in position of the movable part when the proportional valve is close to the closed state results in a first change of the valve opening, and the given change in position of the movable part when the proportional valve is close to the fully open state results in a second change of the valve opening, the second change being greater than the first change.

Thus, the change in valve position may be controlled differently depending on the position of the movable part. That is, when the movable part is close to the closed state, a change in position of the movable part will result in a relatively small increase in the valve opening, implying that a precise flow control is possible even though the difference in pressure inside and outside the chamber is large. On the other hand, when the movable part is close to the fully open state, the same change in position of the movable part will result in a relatively large increase in the valve opening, implying that a rapid evacuation of the chamber is possible even though the difference in pressure inside and outside the chamber is small. For example, after the objects have been sterilized, the pressure inside the chamber is close to the maximum pressure in the sterilization scheme. Hence, the difference in pressure inside the chamber and the pressure outside the chamber is at its largest point, and a small increase in the valve opening will results in a large increase of fluid flow out of the chamber and thus a large pressure drop inside the chamber. A large pressure drop may imply that components inside the chamber may be harmed. Also, the boiling point of a fluid contained inside an open container in the chamber may be reached and that fluid may be spattered inside the chamber. Such a large pressure drop is therefore undesired. By having a proportional valve which may control the valve opening differently depending on the position of the movable part, as described above, such a large pressure drop may be avoided. Furthermore, when the pressure inside the chamber has been reduced, the risk of large pressure drops inside the chamber in response to fluid flow out of the chamber is reduced since the pressure difference inside and outside of the chamber is smaller. Hence, it is desired to increase the fluid flow out of the chamber in order to minimize the process time. By having a proportional valve which may allow for a large valve opening and a large discharge of flow out of the chamber as described above, such desired features may be achieved.

According to at least one embodiment of the invention, the drain inlet, the first conduit, the second conduit and the drain outlet may be comprised in a cast manifold. Hereby a compact design is achieved. Hence, the drain system will occupy less space and may thus be adapted to various different types of sterilization apparatus. Also, the manufacturing cost of the drain system may be reduced since less material is needed.

According to at least one embodiment of the invention, the proportional valve may be connected to the cast manifold. According to at least one embodiment of the invention, the further valve may be connected to the cast manifold. For example, actuators of the proportional valve and the further valve may be directly mounted on the cast manifold. Hereby an even more compact design is achieved.

According to further embodiments, the drain system may further comprise an air detector for detecting non-condensable gases. Having an air detecting system in the drain system may help to early detect if non-condensable gases are present inside the chamber. Non-condensable gases may hinder the sterilization medium inside the chamber to reach the object and thereby preventing a complete sterilization of the objects. Non-condensable gases are therefore undesired inside the chamber. The air detector may be comprised in the cast manifold, possibly connected to the first conduit. Hereby, the air detector may be comprised in the drain system in a compact manner.

According to further embodiments, the drain system may comprise a steam supplier for supplying steam to the chamber for sterilizing bio-hazardous waste inside said chamber. The steam supplier may be connected to a steam generator, wherein the steam generator supplies the steam to the steam supplier. Thus, the steam supplier may provide for an additional path for steam to the chamber compared to the conventional inlet of the sterilization medium to the chamber. The bio-hazardous waste may be any material comprising an infectious substance.

According to at least one embodiment of the invention, the sterilization medium may be steam and/or superheated water. Hereby, a cheap and easy handled sterilization medium is achieved. According to another embodiment of the invention, the sterilization medium may be formalin and/or formaldehyde. Hereby, the sterilization medium may be provided at a lower temperature and/or pressure compared to when steam or superheated water is used.

BRIEF DESCRIPTION OF THE DRAWINGS

These and other aspects of the present invention will now be described in more detail, with reference to the appended drawings showing example embodiments of the invention, wherein:

FIG. 2b is a plane cutaway view of the drain system in FIG. 2a;

DETAILED DESCRIPTION OF AN EXAMPLE EMBODIMENT

In the following description, the present invention is mainly described with reference to a sterilization apparatus for sterilizing objects inside a chamber, and more particularly to a drain system configured to discharge fluid from the chamber. Furthermore, the invention is described with reference to the control of a proportional valve comprised in the drain system in accordance with a predefined sterilization process.

It should, however, be noted that this description by no means limits the scope of the invention, which is equally applicable to, for example, drain systems with other configurations using a proportional valve for discharging fluid from a chamber according to a predefined sterilization process.

Figure 1:
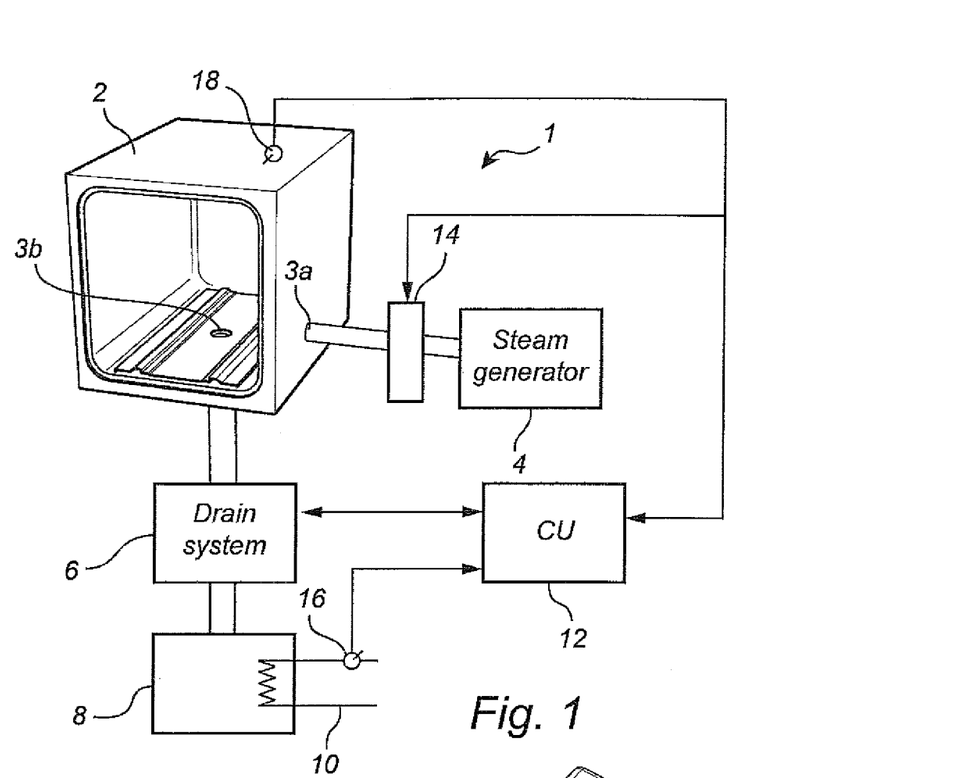
FIG. 1 is a block diagram schematically illustrating a sterilization apparatus.

FIG. 1 illustrates an exemplary sterilization apparatus 1 for sterilizing objects using a sterilization medium, such as a fluid e.g. steam, superheated water, formalin or formaldehyde. The sterilization apparatus 1 comprises a chamber 2 having an inlet 3a and an outlet 3b, a steam generator 4 connected to the inlet 3a, a drain system 6 connected to the outlet 3b, a vacuum system 8 connected to the drain system 6, a flow of coolant 10 connected to the vacuum system 8, a controllable inlet 14 connected to the steam generator 4 and the inlet 3a, and a control unit 12 connected to the drain system 6, the controllable inlet 14, a temperature sensor 16 in the flow of coolant 10, and a pressure sensor 18 in the chamber 2. The steam generator 4 may be integrated in the sterilization apparatus 1 or it may be provided externally.

The drain system 6 is arranged for being able to control the discharge of the fluid, e.g. steam from the chamber 2 through the drain system 6, and the vacuum system 8 is arranged for evacuating the steam from the chamber 2 and condensing the evacuated steam using the flow of coolant 10. The vacuum system 8 may comprise a heat exchanger, such as e.g. a condenser. The vacuum system 8 may comprise a pump, such as e.g. a vacuum pump. Moreover, the vacuum system 8 may comprise both a heat exchanger and a pump, such as e.g. both a condenser and a vacuum pump.

The control unit 12 controls the flow of steam to the chamber 2 from the steam generator 4 via the controllable inlet 14, and the discharge of steam from the chamber 2 to the vacuum system 8 via the drain system 6. As illustrated in FIG. 1, the control unit 12 receives a signal from the temperature sensor 16 arranged to detect the temperature in the flow of coolant 10 after the flow of coolant has been used to cool the fluid in the vacuum system 8. Hereby, the control unit 12 may control the drain system 6 and/or the controllable inlet 14 in order to provide for steam inlet/outlet to and/or from the chamber 2 in accordance with a predefined sterilization scheme and where there is a restrain on the maximum temperature of the coolant flow 10. For example, the control unit 12 may use the information received from the temperature sensor 16 to allow the controllable inlet 14 to admit steam to enter the chamber 2. Likewise, the control unit 12 may use the information received from the temperature sensor 16 to allow the drain system 6 to admit steam/condensate to exit the chamber 2. A scenario where the control unit 12 controls both the controllable inlet 14 and the drain system 6 simultaneously and/or subsequently is also possible. Of course, the control unit 12 may receive other signals as inputs than the temperature in the flow of coolant 10, such as e.g. the pressure inside the chamber 2 using the pressure sensor 18 arranged to detect the pressure inside the chamber 2.

Figure 2A:
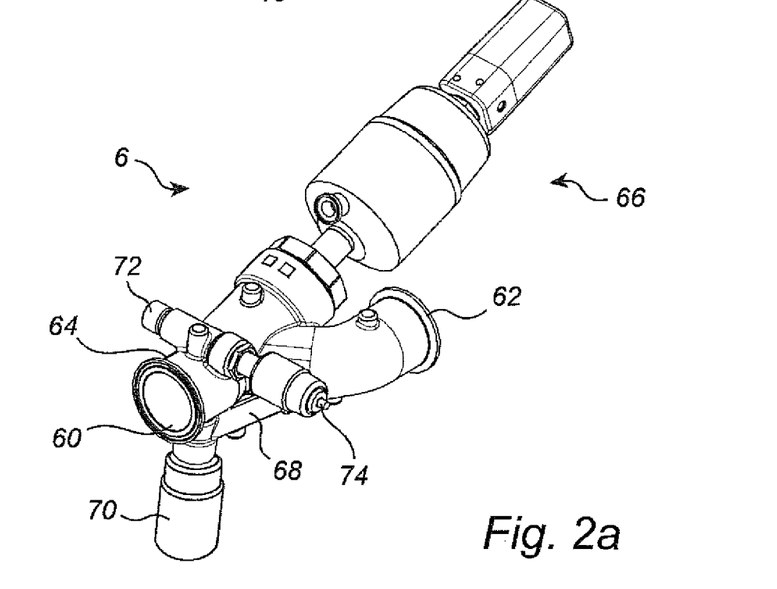
FIG. 2a is a perspective view of an exemplary drain system.

The drain system 6 will now be described in greater detail with reference to FIG. 2a. FIG. 2a illustrates an exemplary drain system 6 comprising a drain inlet 60 for connection with chamber 2, a drain outlet 62 for connection to the vacuum system 8, a first conduit 64 connecting the drain inlet 60 and the drain outlet 62, a proportional valve 66 arranged along the first conduit 64, a second conduit 68, separated from the first conduit 64, connecting the drain inlet 60 and the drain outlet 62, and a further valve 70 arranged along the second conduit 68. As illustrated in FIG. 2a, the drain system may further comprise couplings 72, 74 for connecting additional components, such as e.g. an air detector (not shown) for detecting non-condensable gases in the chamber 2 and in the drain system 6, or a steam supplier (not shown) for supplying steam into the chamber 2 for sterilizing bio-hazardous waste inside the chamber 2.

Figure 2B:
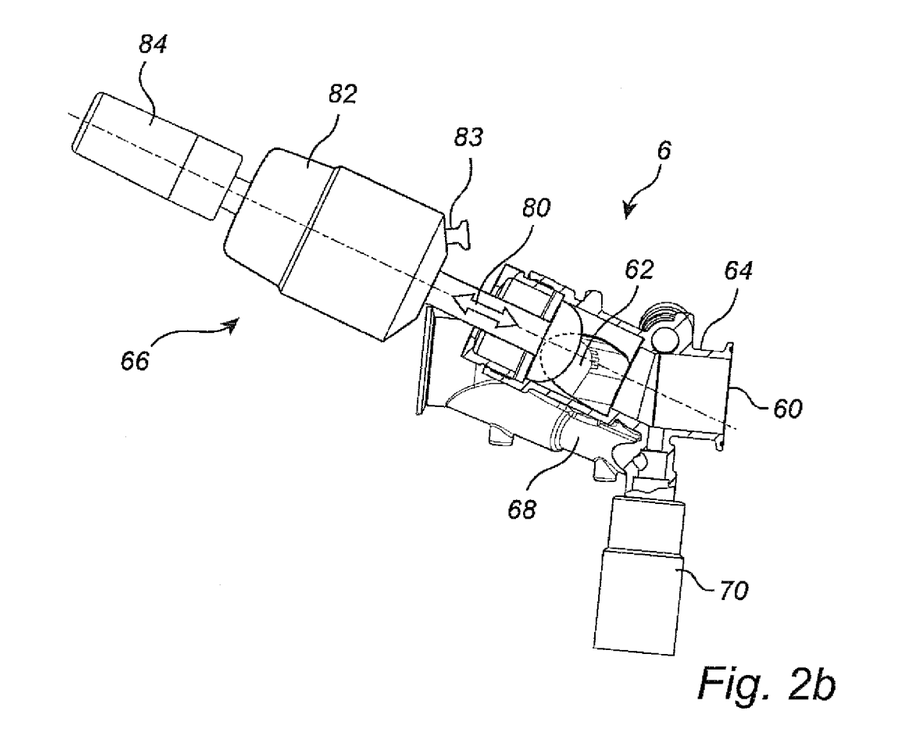

In FIG. 2b, which is a plane cutaway view of a part of the drain system 6, the interior of the proportional valve 66 is shown. As illustrated in FIG. 2b, the proportional valve 66 comprises a movable part 80, an actuator 82, a pneumatic air connection 83, and a valve control unit 84. Furthermore, in FIG. 2b, the further valve 70 connected to the second conduit 68 is shown.

The movable part 80 restricts the fluid flow through the first conduit 64 as the fluid flows from the drain inlet 60 to the drain outlet 62. The movable part 80 is controlled by the actuator 82 and the valve control unit 84. The valve control unit 84 is controlling air flow through the pneumatic air connection 83 to and from the actuator 82 in such way that the movable part 80 may move between a closed state and a fully open state. The second conduit 68 is in the illustration in FIG. 2b arranged in parallel with the first conduit 64, thus allowing a fluid flow to bypass the proportional valve 66. The fluid flow through the second conduit 68 is controlled by the further valve 70. The further valve 70 may be a digital valve.

Figure 3:
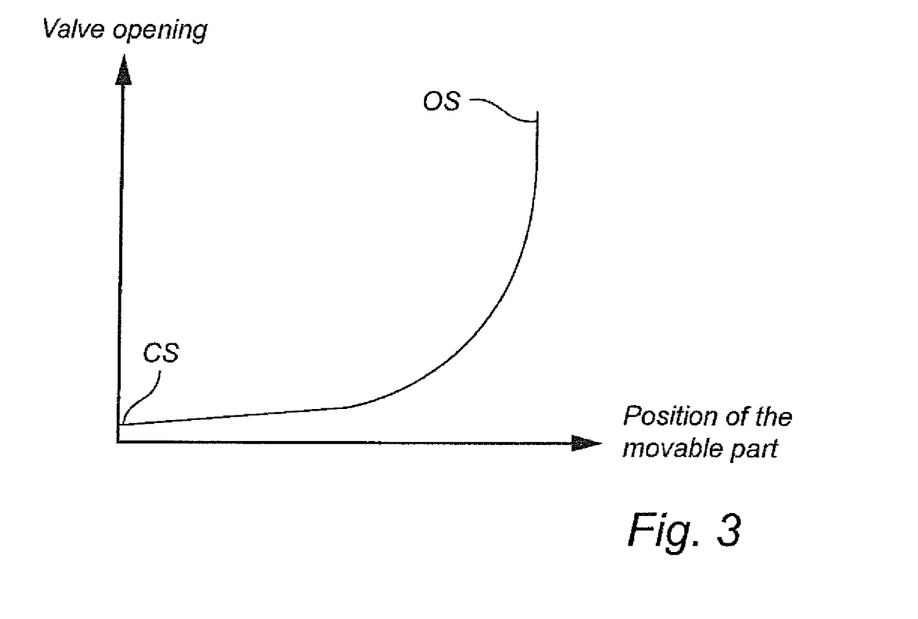
FIG. 3 is a graph illustrating the valve characteristic in the drain system.

The proportional valve 66 will now be described in greater detail with reference to FIG. 3. FIG. 3 is a graph showing the relation between the valve opening (Y-axis) and the position of the movable part 80 (X-axis). It should be understood that the valve opening is the opening defined by the movable part 80 and the first conduit 6 as seen from the drain inlet 60 to the drain outlet 62. Furthermore, it should be noted that the position of the movable part 80 may move between a closed state CS and a fully open state OS of the proportional valve 66.

As illustrated in FIG. 3, the proportional valve 66 has the characteristic that for a given change in the position of the movable part 80, when the proportional valve 66 is close to the closed state CS results in a first change of the valve opening. The same change in the position of the movable part 80, when the proportional valve 66 is close to the fully open state OS results in a second change of the valve opening. As illustrated in the graph, the second change is greater than the first change.

This implies that the fluid flow through the first conduit 64 may be controlled differently depending on the position of the movable part 80. For example, when the movable part 80 is close to the closed state CS, a change in position of the movable part 80 will result in a relative small change of the valve opening, implying that a precise flow control is possible through the first conduit 64 even though the difference in pressure inside and outside the chamber 2 is large. On the other hand, when the movable part 80 is close to the fully open state OS, the same change in position of the movable part 80 will result in a relative large change of the valve opening, implying that a rapid evacuation of the chamber 2 is possible even though the difference in pressure inside and outside the chamber 2 is small. Owing to this, the proportional valve 66 having a characteristic as shown in FIG. 3 implies that the magnitude in the change of the valve opening is less dependent on a change in position of the movable part 80 when the proportional valve 66 is close to its closed state SC compared to when the proportional valve 66 is close to its fully open state OS.

Figure 4:
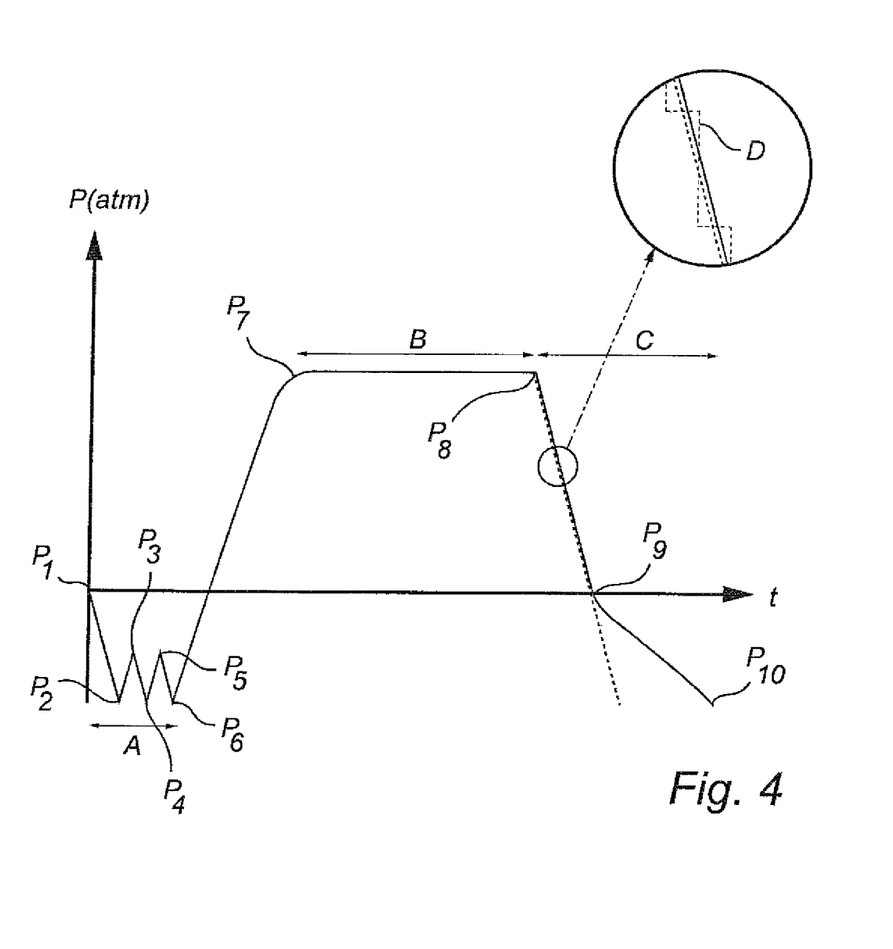
FIG. 4 is a graph illustrating an exemplary sterilization process.

FIG. 4 is a graph illustrating a schematic example of a sterilization process scheme by describing the relation between pressure P inside the chamber 2 (Y-axis) and time t (X-axis). The X-axis intersects with the Y-axis at the chamber pressure of 1 atm, implying a pressure below atmospheric pressure below the X-axis. The solid line in the graph represents an example sterilization process scheme controlled by the control unit 12, and the thick dashed line represents an ideal decrease of pressure during the discharge of fluid out of the chamber 2 to the vacuum system 8, which is comprised by e.g. a condenser and/or a vacuum pump, via the drain system 6 controlled by the proportional valve 66. The ideal decrease of pressure is represented by a sterilization scheme in accordance with the European standard EN285, described above. The thin dashed line represents the behavior of pressure during the discharge of fluid out of the chamber 2a using a conventional drain system with one or several digital valves. Steam is used as sterilization medium and the vacuum system 8 is connected to a flow of coolant 12 similar to what was described above in connection with FIG. 1.

Part A in FIG. 4 represents the part of the sterilization scheme where air and steam are evacuated from the chamber 2 and where steam is partly introduced into the chamber 2. This part is represented by three minima of the solid line where the pressure inside the chamber is at its lowest points P2, P4, P6. In the first pressure reduction, represented by the solid line ranging from point P1 to point P2 in the graph, only air is evacuated from the chamber 2 by using e.g. a vacuum pump. Subsequently, steam is introduced into the chamber 2, raising the pressure inside the chamber 2, represented by the solid line ranging from point P2 to point P3. Then, more air, and some of the steam introduced in the previous step, are evacuated from the chamber 2, represented by the solid line ranging from point P3 to point P4. These procedures, introducing steam to the chamber 2 and subsequently evacuating air and/or steam from the chamber 2 may be followed by one or more similar steps, represented e.g. by the solid line ranging from point P4 to P5 to P6, until substantially no air is present inside the chamber 2.

When substantially no air is present inside the chamber 2, more steam is introduced into the chamber 2, represented by the solid line ranging from point P6 to point P7. Part B (the solid line ranging from point P7 to point P8) represents the part of the sterilization scheme where steam has been introduced into the chamber 2 and where temperature and pressure inside the chamber 2 are high enough for the sterilization of the objects to occur. The sterilization temperature may be e.g. a temperature between 105° C. and 140° C., such as 121° C. For example, the sterilization temperature may be 121° C. in 15 minutes.

Part C represents the part of the sterilization scheme where steam is discharged from the chamber 2 to the vacuum system 8 via the drain system 6 using the proportional valve 66.

As illustrated in the enlarged view in FIG. 4, for a sterilization apparatus with a conventional drain system using a digital valve, the decrease in pressure is carried out in a stepwise manner (thin dashed line) during the discharge of steam from the chamber 2, since no continuous control of the fluid flow through the drain system is possible. Instead, the thin dashed line represents a digital valve which is alternating between a closed state and an open state. This type of valve behavior results in a decrease of the pressure inside the chamber 2 by a series of pressure drops D. As illustrated in the enlarged view in FIG. 4, the pressure drops D may lower the pressure inside the chamber with a rate of pressure change which deviates from the ideal decrease of the pressure. Such pressure drops D may result in that components inside the chamber may be harmed and/or that the boiling point of a fluid contained in an open container inside the chamber may be reached and that fluid may be spattered inside the chamber.

By having a proportional valve 66 which may control the fluid flow differently depending on the position of the movable part 80, as described above with reference to FIGS. 2 and 3, such pressure drops D may be avoided. Accordingly, the decrease in pressure during the discharge of steam from the chamber 2 may follow the ideal decrease in pressure as indicated by the solid line, if a proportional valve 66 is used in the drain system 6.

The part of the curve furthest to the right, where the process scheme, represented by the solid line ranging from point P9 to point P10, diverges from the ideal decrease of pressure, may represent a process scheme where the discharge of fluid from the chamber is restricted by e.g. the temperature of the cooling flow 10. If the temperature of the cooling flow 10 is approaching its maximum limit, the control unit 12 may detect the temperature by the temperature sensor 16 and control the proportional valve 66 to reduce the valve opening in the first conduit 64. Hence, the fluid flow out of the chamber and to the vacuum system 8 via the drain system 6 may be reduced. Thus, less energy needs to be withdrawn from the vacuum system 8 by the coolant flow 10 and the temperature of the coolant flow 10 may be prevented from increasing above the maximum limit.

Additionally, variations to the disclosed embodiments can be understood and effected by the skilled person in practicing the claimed invention, from a study of the drawings, the disclosure, and the appended claims. For example, the drain system may comprise a proportional valve with a different characteristic than presented here, which may vary the valve opening in the first conduit in a different way.

In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

The invention claimed is:

1. A sterilization apparatus for sterilization of objects, said sterilization apparatus comprising:
   a chamber for receiving said objects to be sterilized, said chamber including a sterilization medium inlet and a sterilization medium outlet;
   an inlet flow control device connected to said sterilization medium inlet for controlling a supply of a sterilization medium to said chamber;
   a sterilization medium providing device connected to said sterilization medium inlet for providing the sterilization medium to said chamber;
   a drain system connected to said sterilization medium outlet of the chamber for controllable discharge of fluid from said chamber;
   a vacuum system including a heat exchanger configured to reduce a temperature of the fluid from the drain system, and a temperature sensor configured to measure a temperature of a flow of coolant after the flow of coolant has been used to cool the fluid via the heat exchanger, wherein the flow of coolant has a separate path from, and does not mix with, the fluid received from the drain system; and
   a control unit connected to the vacuum system and the drain system, and configured to control said drain system in accordance with a sterilization scheme;
   wherein the drain system includes:
      a drain inlet connected to said sterilization medium outlet of the chamber;
      a drain outlet connected to the vacuum system for evacuating the chamber;
      a first conduit connecting said drain inlet and said drain outlet; and
      a proportional valve arranged along said first conduit, said proportional valve being controllable by said control unit to control fluid flow through said first conduit;
      wherein the proportional valve includes a movable part;
      wherein a size of the valve opening is continuously adjustable based on a continuous movement of the movable part; and
   wherein the control unit is configured to control, based on the temperature of the flow of coolant received from the temperature sensor, the proportional valve included in the drain system to control the discharge of the fluid from the chamber, including by restricting discharge of fluid from the chamber in response to the temperature of the flow of coolant approaching a maximum allowable temperature.

2. The sterilization apparatus according to claim 1, wherein the sterilization medium providing device is a steam generator and the sterilization medium comprises steam; and
   wherein the heat exchanger is a condenser adapted for condensing steam.

3. The sterilization apparatus according to claim 1, wherein the control unit is configured to maintain the temperature of the coolant within a selected range by controlling the proportional valve to thereby control discharge of fluid from the chamber.

4. The sterilization apparatus according to claim 1, further comprising a second conduit separated from said first conduit, connecting said drain inlet and said drain outlet, and a further valve arranged along said second conduit to allow control of a flow through said second conduit.

5. The sterilization apparatus according to claim 4, wherein a cross section of said second conduit is smaller than a cross section of said first conduit.

6. The sterilization apparatus according to claim 1, wherein said proportional valve includes a controllable actuator connected to said movable part for controlling a position of said movable part between a closed state and a fully open state.

7. The sterilization apparatus according to claim 6, wherein said proportional valve is configured in such a way that a given change in position of said movable part when the proportional valve is close to the closed state results in a first change of said valve opening, and said given change in position of said movable part when the proportional valve is close to said fully open state results in a second change of said valve opening, said second change being greater than said first change.

8. The sterilization apparatus according to claim 4, wherein said drain inlet, said first conduit, said second conduit and said drain outlet are included in a cast manifold.

9. The sterilization apparatus according to claim 1, the proportional valve being controllable by said control unit to control fluid flow through said first conduit according to a continuous relation between a control parameter and a valve opening of said proportional valve.

10. The sterilization apparatus according to claim 1, wherein the movable part is movable between a closed state in which the valve opening is closed and a fully open state in which the valve opening is fully open.

11. The sterilization apparatus according to claim 10, wherein:
    when the movable part is near the closed state, an amount of movement of the movable part will result in a first change of size of the valve opening; and
    when the movable part is near the fully open state, the amount of movement of the movable part will result in a second change of size of the valve opening that is different from the first change of size of the valve opening.

12. The sterilization apparatus according to claim 11, wherein the first change of size of the valve opening is smaller than the second change of size of the valve opening.

13. A sterilization apparatus for sterilization of objects, comprising:
    a chamber for receiving objects to be sterilized, the chamber including a sterilization medium inlet and a sterilization medium outlet;
    a sterilization medium providing device connected to the sterilization medium inlet for providing the sterilization medium to the chamber;
    a drain system connected to the sterilization medium outlet of the chamber for controllable discharge of fluid from the chamber;
    a vacuum system including a heat exchanger configured to cool the fluid received from the drain system, and a temperature sensor configured to measure a temperature of a flow of coolant used by the heat exchanger, wherein the flow of coolant in the sterilization apparatus is fully separate from the fluid received from the drain system; and a control unit connected to the drain system and configured to control the drain system;
wherein the drain system includes:
  a drain inlet connected to the sterilization medium outlet of the chamber;
  a drain outlet connected to the vacuum system for evacuating the chamber;
  a first conduit connecting the drain inlet and the drain outlet; and
  a proportional valve disposed along the first conduit, the proportional valve being controllable by said control unit to control fluid flow through said first conduit based on a valve opening of the proportional valve;
wherein the proportional valve includes a movable part;
wherein a size of the valve opening is continuously adjustable based on a continuous movement of the movable part;
wherein when the movable part is near a closed state, an amount of movement of the movable part will result in a first change of size of the valve opening;
wherein when the movable part is near the fully open state, the amount of movement of the movable part will result in a second change of size of the valve opening that is larger than the first change of size of the valve opening; and
wherein the control unit is configured to receive the temperature of the flow of coolant from the temperature sensor, and to control, based on the temperature of the coolant, the proportional valve so as to control the discharge of the fluid out of the chamber.

14. The sterilization apparatus according to claim 13, further comprising an air detector for detecting non-condensable gases.

15. The sterilization apparatus according to claim 13, the drain system further comprising a second conduit separated from said first conduit, connecting said drain inlet and said drain outlet, and a further valve arranged along said second conduit to allow control of a flow through said second conduit.

16. The sterilization apparatus according to claim 13, wherein said sterilization medium is at least one of steam and superheated water.

17. The sterilization apparatus according to claim 13, wherein said sterilization medium is at least one of formalin and formaldehyde.

18. A sterilization apparatus for sterilization of objects, comprising:
  a chamber for receiving objects to be sterilized, the chamber including a sterilization medium inlet and a sterilization medium outlet;
  a sterilization medium providing device connected to the sterilization medium inlet for providing the sterilization medium to the chamber;
  a drain system connected to the sterilization medium outlet of the chamber for controllable discharge of fluid from the chamber, the drain system including a valve configured to control the discharge of the fluid from the chamber based on a valve opening of the valve;
  a vacuum system including a heat exchanger configured to reduce a temperature of the fluid from the drain system, and a temperature sensor configured to measure a temperature of a flow of coolant after the coolant exchanges heat with the fluid, wherein the flow of coolant in the sterilization apparatus is separated from and does not mix with said fluid from the drain system; and
  a control unit coupled to the vacuum system and the drain system, the control unit being configured to control the valve based on the temperature of the flow of coolant;
  wherein controlling the valve controls the discharge of the fluid from the chamber.

19. The sterilization apparatus according to claim 18, wherein the control unit is configured to control the valve to reduce a flow of the discharge of the fluid from the chamber, when the temperature of the coolant is over a predetermined temperature.

20. The sterilization apparatus according to claim 18, wherein the drain system comprises:
  a first conduit connecting a drain inlet and a drain outlet;
  a second conduit connecting said drain inlet and said drain outlet;
  the valve arranged along the first conduit;
  a further valve arranged along the second conduit; and
  wherein the valve and the further valve are configured to control passage of fluid between the chamber and the vacuum system.

* * * * *